(12) United States Patent
Olson et al.

(10) Patent No.: US 7,615,040 B2
(45) Date of Patent: Nov. 10, 2009

(54) THIN, FLEXIBLE, LOW CAPACITY ABSORBENT ARTICLE WITH LEAKAGE PROTECTION

(75) Inventors: Christopher Peter Olson, Neenah, WI (US); Lawrence Howell Sawyer, Neenah, WI (US); Shirlee Ann Weber, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 1935 days.

(21) Appl. No.: 10/025,173

(22) Filed: Dec. 19, 2001

(65) Prior Publication Data
US 2003/0125689 A1    Jul. 3, 2003

(51) Int. Cl.
*A61F 13/15* (2006.01)
(52) U.S. Cl. .................. 604/385.101; 604/378; 604/368; 604/379; 604/380
(58) Field of Classification Search .......... 604/385.101, 604/378, 385.01, 379, 380, 367, 368, 385.23
See application file for complete search history.

(56) References Cited

U.S. PATENT DOCUMENTS

| | | | |
|---|---|---|---|
| 3,338,992 A | 8/1967 | Kinney | |
| 3,341,394 A | 9/1967 | Kinney | |
| 3,502,538 A | 3/1970 | Petersen | |
| 3,502,763 A | 3/1970 | Hartmann | |
| 3,542,615 A | 11/1970 | Dobo et al. | |
| 3,692,618 A | 9/1972 | Dorschner et al. | |
| 3,802,817 A | 4/1974 | Matsuki et al. | |
| 3,849,241 A | 11/1974 | Butin et al. | |
| 4,340,563 A | 7/1982 | Appel et al. | |
| 4,619,649 A | 10/1986 | Roberts | |
| 4,663,220 A | 5/1987 | Wisneski et al. | |
| 4,704,116 A | 11/1987 | Enloe | |
| 4,940,464 A | 7/1990 | Van Gompel et al. | |
| 5,046,272 A | 9/1991 | Vogt et al. | |
| 5,061,259 A | 10/1991 | Goldman et al. | |
| 5,062,839 A | 11/1991 | Anderson | |
| 5,098,423 A * | 3/1992 | Pieniak et al. | 604/385.27 |
| 5,104,116 A | 4/1992 | Pohjola | |
| 5,224,405 A | 7/1993 | Pohjola | |
| 5,226,992 A | 7/1993 | Morman | |
| 5,342,343 A | 8/1994 | Kitaoka et al. | |
| 5,354,289 A | 10/1994 | Mitchell et al. | |

(Continued)

FOREIGN PATENT DOCUMENTS

EP    0 217 032    4/1987

(Continued)

OTHER PUBLICATIONS

Japanese Official Action issued Sep. 8, 2008, 2 pages.

*Primary Examiner*—Jacqueline F. Stephens
(74) *Attorney, Agent, or Firm*—Armstrong Teasdale, LLP

(57) ABSTRACT

An absorbent article having a thin, flexible absorbent pad that can accommodate one or two insults with a low probability of leakage. The absorbent article can be less than about 5 millimeters thick, with the absorbent pad being less than about 3 millimeters thick. The absorbent article has a low absorbent capacity of, for example, less than three times an anticipated single insult volume, or less than twice an anticipated single insult volume. The absorbent article is particularly suitable for use as a toilet training aid.

62 Claims, 5 Drawing Sheets

U.S. PATENT DOCUMENTS

| | | | |
|---|---|---|---|
| H1376 H | 11/1994 | Osborn, III et al. | |
| 5,562,645 A * | 10/1996 | Tanzer et al. | 604/367 |
| 5,658,268 A | 8/1997 | Johns et al. | |
| 5,728,082 A | 3/1998 | Gustafsson et al. | |
| 5,797,892 A | 8/1998 | Glaug et al. | |
| 5,820,973 A | 10/1998 | Dodge, II et al. | |
| 5,994,614 A * | 11/1999 | Wada et al. | 604/378 |
| 5,994,615 A | 11/1999 | Dodge, II et al. | |
| 6,068,620 A | 5/2000 | Chmielewski | |
| 6,152,904 A | 11/2000 | Matthews et al. | |
| 6,168,585 B1 * | 1/2001 | Cesco-Cancian | 604/385.26 |
| 6,287,287 B1 * | 9/2001 | Elsberg | 604/385.03 |
| 6,320,096 B1 | 11/2001 | Inoue et al. | |
| 6,465,712 B1 | 10/2002 | Matthews et al. | |
| 6,646,180 B1 | 11/2003 | Chmielewski | |
| 2002/0156441 A1 | 10/2002 | Sawyer et al. | |

FOREIGN PATENT DOCUMENTS

| | | |
|---|---|---|
| EP | 0 304 319 A2 | 2/1989 |
| GB | 2 063 683 A | 6/1981 |
| JP | H05-504083 | 7/1993 |
| JP | H10-234778 | 9/1998 |
| JP | 2002509764 | 4/2002 |
| JP | 2002238934 | 8/2002 |
| WO | 9111978 | 8/1991 |
| WO | WO 92/07534 | 5/1992 |
| WO | 94/10958 | 5/1994 |
| WO | 9822067 | 5/1998 |
| WO | 9949826 | 10/1999 |
| WO | 01/00117 | 1/2001 |
| WO | WO 01/34082 A1 | 5/2001 |
| WO | 02049565 | 6/2002 |

\* cited by examiner

THIN, FLEXIBLE, LOW CAPACITY ABSORBENT ARTICLE WITH LEAKAGE PROTECTION

BACKGROUND OF THE INVENTION

This invention is directed to an absorbent article, such as a pant-like absorbent article, that can accommodate one or two insults with a low probability of leakage.

Relatively thick absorbent composites are often used in disposable absorbent garments, such as diapers. However, in recent years it has become increasingly desirable to produce absorbent composites which are thin compared to the more traditional absorbent composites but which still possess absorbent capacity and leakage protection. In particular, when a child begins toilet training, the toilet training process may be hampered by the child's inability to discern the difference between diapers and training pants if the training pants are as thick and cumbersome as the diapers. If the training pants appear to be too diaper-like, the child may not be motivated to participate in the toilet training process. Thin absorbents provide for a greater garment-like appearance as well as improved discretion when worn under other garments. The desire to achieve a more grown-up appearance with a training pant having a thinner absorbent may motivate a child to participate in the toilet training process.

During the toilet training process, a child may be particularly motivated to become fully toilet-trained if his or her training pants hold only a limited amount of waste. More particularly, if a training pant is designed to absorb multiple insults, the child may not be as aware of having urinated and may not be as motivated to change his or her training pant immediately after the first insult. However, if a training pant is designed to hold only one or two insults, the child may be more likely to realize immediately after a first insult that a clean training pant should be applied in order to avoid any embarrassing leakage that would occur after multiple insults.

Leakage protection is very important in training pants designed to hold only one or two insults. If a training pant leaks after only one insult or at low volumes of urine, the child may become frustrated thus perceiving the act of changing the training pant as futile since the garment is destined to leak regardless of the number or amount of insults. Furthermore, leakage protection in a training pant having limited absorbent capacity benefits the wearer by providing a safeguard against embarrassing leakage after a first insult, and also benefits a caregiver by preventing extra work and stains in the wearer's clothing if the wearer informs the caregiver of the need to change the training pant after the first insult. If the wearer of a training pant having limited absorbent capacity and leakage protection exceeds the capacity of the pant by issuing multiple insults, the wearer not only experiences unavoidable leakage due to the excessive urine volume but also incurs disappointment from the caregiver, thus giving the training pant wearer an incentive to become toilet trained.

There is a need or desire for a low capacity disposable absorbent article that is capable of absorbing only one or two insults and preventing leakage of one or two insults.

There is a further need or desire for a toilet training garment that motivates a child to complete the toilet training process without discouraging the child.

SUMMARY OF THE INVENTION

In response to the discussed difficulties and problems encountered in the prior art, a new thin, flexible, low capacity absorbent article has been discovered.

The present invention is directed to a disposable absorbent article having a thin, flexible absorbent pad that can accommodate one or two insults with a low probability of leakage. The absorbent pad can be located between an outer cover and a body side liner, possibly with a surge layer between the absorbent pad and the body side liner. The absorbent article is designed to function over a wide range of user activities and positions while providing a thin, garment-like appearance.

The absorbent article is particularly suitable for use as a toilet training aid. The thinness of the absorbent pad enables a child to see the benefit of a training pant including such an absorbent pad, compared to a conventional, bulky diaper. The training pant including the thin absorbent pad looks more like "big kid" underwear than a bulky diaper, and is more discreet underneath clothing than a bulky diaper. The absorbent pad itself is suitably less than about 2 millimeters thick, and the entire absorbent article is suitably less than about 3 millimeters thick.

The low absorbent capacity of the absorbent article of the invention may motivate a child to change into a clean training pant immediately after issuing an insult into the training pant. Through experience, the child is likely to realize that the low capacity training pant will overflow and create a situation with consequences if multiple insults are dispensed within the training pant. By bringing about such awareness in the child, the child is likely to soon thereafter become aware of impending insults he or she is about to issue, and therefore complete the toilet training process.

The absorbent article of the invention provides leakage protection for most single insult volumes and at least up to a significant part of the article's saturated capacity. Leakage protection provides a sense of security to the wearer after the first insult, allowing the wearer time to change into a clean absorbent article. In other words, a child can experience the consequences of wetting without the necessity of the caregiver also experiencing the negative consequences. If the wearer ignores the first insult and continues to issue multiple insults, the absorbent article will leak, causing discomfort for the wearer as well as for the caregiver. This combination of cause and effect can help motivate children to toilet train. The concept is simple and straightforward so it is easy for a toddler to understand.

With the foregoing in mind, particular embodiments of the invention provide an absorbent article that provides comfort, discretion, and leakage protection during use situations where single voids may be anticipated.

Additionally, particular embodiments of the invention provide a toilet training garment that motivates a child to complete the toilet training process without discouraging the child.

DEFINITIONS

Figure 1:
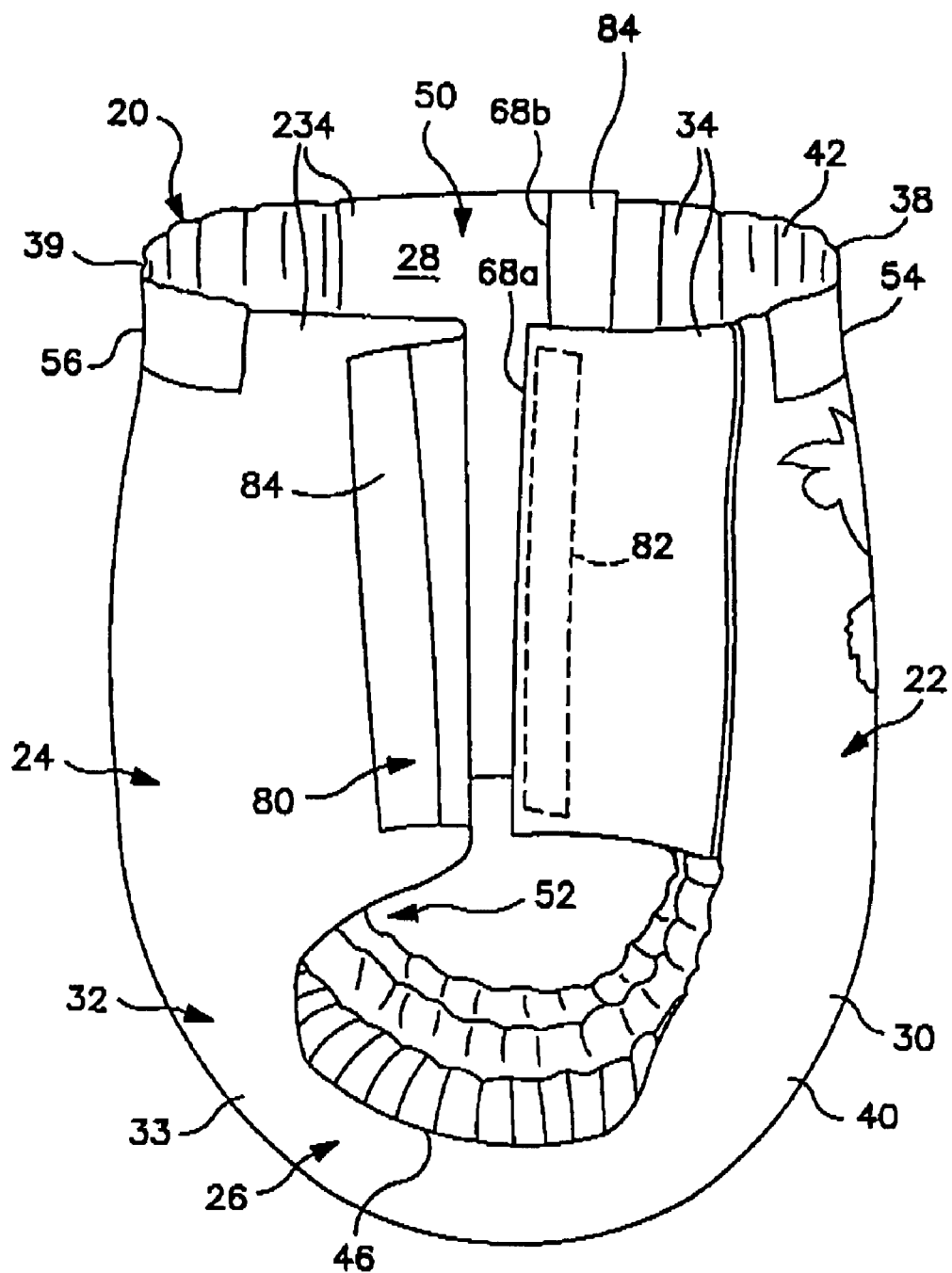
FIG. 1 is a side perspective view of an absorbent garment having a low capacity absorbent pad, according to one embodiment of this invention.

Within the context of this specification, each term or phrase below will include the following meaning or meanings.

"Absorbent capacity" refers to the maximum volume of liquid that can be absorbed by a product as measured by the Saturated Capacity Test.

"Anticipated single insult volume" refers to the amount of urine or other exudates that can be expected to be expelled during a single void or insult, typically based on an average of acquired data.

"Bonded" refers to the joining, adhering, connecting, attaching, or the like, of two elements. Two elements will be considered to be bonded together when they are bonded directly to one another or indirectly to one another, such as when each is directly bonded to intermediate elements.

"Disposable" refers to garments or articles which are designed to be discarded after a limited use rather than being laundered or otherwise restored for reuse.

"Disposed," "disposed on," and variations thereof are intended to mean that one element can be integral with another element, or that one element can be a separate structure bonded to or placed with or placed near another element.

"Elastic," "elasticized" and "elasticity" mean that property of a material or composite by virtue of which it tends to recover its original size and shape after removal of a force causing a deformation.

"Elastomeric" refers to a material or composite which can be elongated by at least 25 percent of its relaxed length and which will recover, upon release of the applied force, at least 10 percent of its elongation. It is generally preferred that the elastomeric material or composite be capable of being elongated by at least 100 percent, more preferably by at least 300 percent, of its relaxed length and recover, upon release of an applied force, at least 50 percent of its elongation.

"Fabric" is used to refer to all of the woven, knitted and nonwoven fibrous webs.

"Film" refers to a thermoplastic film made using a film extrusion and/or foaming process, such as a cast film or blown film extrusion process. The term includes apertured films, slit films, and other porous films which constitute liquid transfer films, as well as films which do not transfer liquid.

"Hydrophilic" describes fibers or the surfaces of fibers which are wetted by the aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by a Cahn SFA-222 Surface Force Analyzer System, or a substantially equivalent system. When measured with this system, fibers having contact angles less than 90° are designated "wettable" or hydrophilic, while fibers having contact angles greater than 90° are designated "nonwettable" or hydrophobic.

"Insult liquid volume runoff" refers to the amount of liquid that exceeds the absorbent capacity, or saturated capacity, of a material.

"Integral" or "integrally" is used to refer to various portions of a single unitary element rather than separate structures bonded to or placed with or placed near one another.

"Layer" when used in the singular can have the dual meaning of a single element or a plurality of elements (i.e., an element may consist of multiple layers).

"Liquid-imperneable," when used to describe a layer or laminate means that liquid such as urine will not pass through the layer or laminate under ordinary use conditions in a direction generally perpendicular to the plane of the layer or laminate at the point of liquid contact.

"Liquid-permeable," refers to a layer or laminate that is not liquid impermeable.

Figure 2:
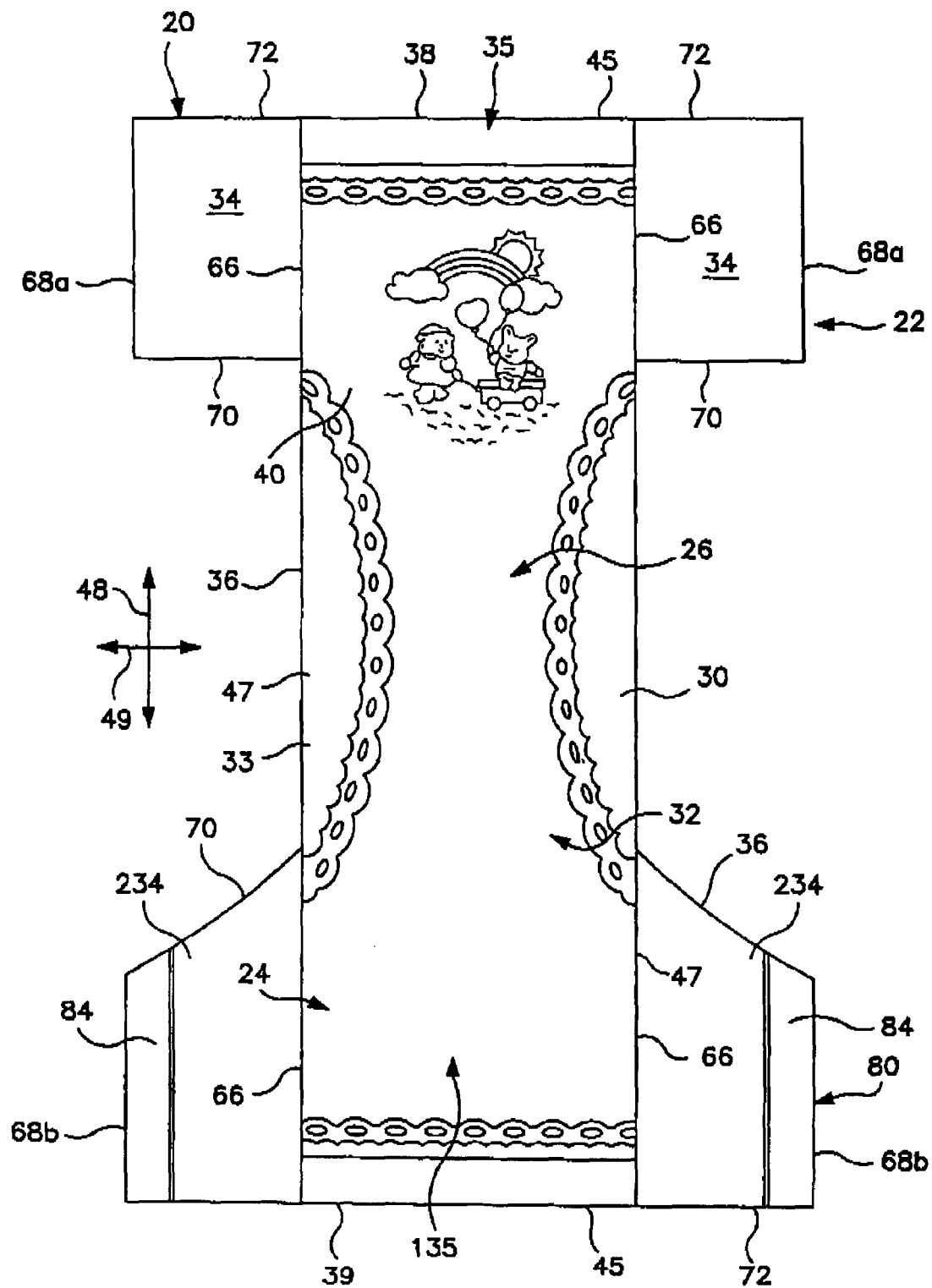
FIG. 2 is a plan view of the absorbent garment of FIG. 1 in a partially disassembled, stretched flat state, and showing the surface of the garment that faces away from the wearer when the garment is worn, according to one embodiment of this invention.
Figure 3:
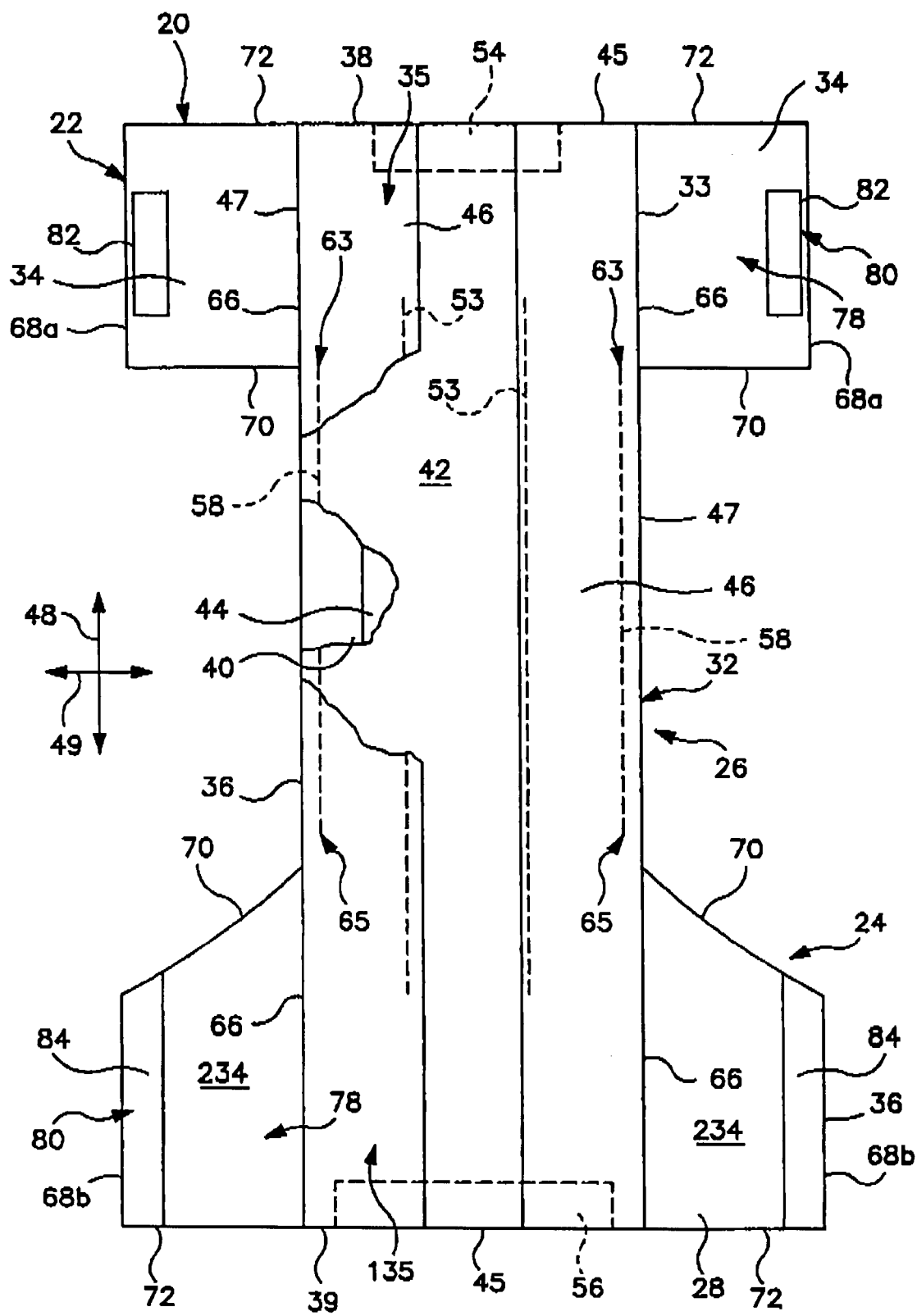
FIG. 3 is a plan view of the absorbent garment of FIGS. 1 and 2 in a partially disassembled, stretched flat state, and showing the surface of the garment that faces the wearer when the article is worn, and with portions cut away to show the underlying features, according to one embodiment of this invention.

"Longitudinal" and "transverse" have their customary meaning, as indicated by the longitudinal and transverse axes depicted in FIGS. 2 and 3. The longitudinal axis lies in the plane of the article and is generally parallel to a vertical plane that bisects a standing wearer into left and right body halves when the article is worn. The transverse axis lies in the plane of the article generally perpendicular to the longitudinal axis. The article as illustrated is longer in the longitudinal direction than in the transverse direction.

"Meltblown fiber" means fibers formed by extruding a molten thermoplastic material through a plurality of fine, usually circular, die capillaries as molten threads or filaments into converging high velocity heated gas (e.g., air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed for example, in U.S. Pat. No. 3,849,241 to Butin et al. Meltblown fibers are microfibers which may be continuous or discontinuous, are generally smaller than about 0.6 denier, and are generally self bonding when deposited onto a collecting surface. Meltblown fibers used in the present invention are preferably substantially continuous in length.

"Member" when used in the singular can have the dual meaning of a single element or a plurality of elements.

"Nonwoven" and "nonwoven web" refer to materials and webs of material which are formed without the aid of a textile weaving or knitting process.

"Operatively joined," in reference to the attachment of an elastic member to another element, means that the elastic member when attached to or connected to the element, or treated with heat or chemicals, by stretching, or the like, gives the element elastic properties; and with reference to the attachment of a non-elastic member to another element, means that the member and element can be attached in any suitable manner that permits or allows them to perform the intended or described function of the joinder. The joining, attaching, connecting or the like can be either directly, such as joining either member directly to an element, or can be indirectly by means of another member disposed between the first member and the first element.

"Permanently bonded" refers to the joining, adhering, connecting, attaching, or the like, of two elements of an absorbent garment such that the elements tend to be and remain bonded during normal use conditions of the absorbent garment.

"Polymers" include, but are not limited to, homopolymers, copolymers, such as for example, block, graft, random and alternating copolymers, terpolymers, etc. and blends and modifications thereof. Furthermore, unless otherwise specifically limited, the term "polymer" shall include all possible geometrical configurations of the material. These configurations include, but are not limited to isotactic, syndiotactic and atactic symmetries.

"Product thickness" refers to the caliper of the thickest portion of the open, laid flat product.

"Refastenable" refers to the property of two elements being capable of releasable attachment, separation, and subsequent releasable reattachment without substantial permanent deformation or rupture.

"Single insult training pant" refers to a training pant designed to retain fewer than two insults.

"Spunbonded fiber" refers to small diameter fibers which are formed by extruding molten thermoplastic material as filaments from a plurality of fine capillaries of a spinnerette having a circular or other configuration, with the diameter of the extruded filaments then being rapidly reduced as by, for example, in U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartmann, U.S. Pat. No. 3,502,538 to Petersen, and U.S. Pat. No. 3,542,615 to Dobo et al., each of which is incorporated herein in its entirety by reference. Spunbond fibers are quenched and generally not tacky when they are deposited onto a collecting surface. Spunbond fibers are generally continuous and often have average deniers larger than about 0.3, more particularly, between about 0.6 and 10.

"Stretchable" means that a material can be stretched, without breaking, to at least 1.2 times of its initial (unstretched) length in at least one direction.

"Superabsorbent" or "superabsorbent material" refers to a water-swellable, water-insoluble organic or inorganic material capable, under the most favorable conditions, of absorbing at least about 15 times its weight and, more desirably, at least about 30 times its weight in an aqueous solution containing 0.9 weight percent sodium chloride. The superabsorbent materials can be natural, synthetic and modified natural polymers and materials. In addition, the superabsorbent materials can be inorganic materials, such as silica gels, or organic compounds such as cross-linked polymers.

"Surface" includes any layer, film, woven, nonwoven, laminate, composite, or the like, whether pervious or impervious to air, gas, and/or liquids.

"Thermoplastic" describes a material that softens when exposed to heat and which substantially returns to a nonsoftened condition when cooled to room temperature.

These terms may be defined with additional language in the remaining portions of the specification.

DETAILED DESCRIPTION OF THE INVENTION

The present invention is directed to an absorbent article, such as a pant-like absorbent garment, that can accommodate one or two insults with a low probability of leakage. The principles of the present invention can be incorporated into any suitable disposable absorbent article. Examples of such suitable articles include diapers, training pants, feminine hygiene products, incontinence products, other personal care or health care garments, or the like. The absorbent article is particularly effective as a training aid when toilet training children. For ease of explanation, the description hereafter will be in terms of a child's training pant.

Referring to FIG. 1, a pant-like disposable absorbent garment or article, such as a training pant 20, is illustrated in a partially fastened condition. The training pant 20 includes a chassis 32 and a fastening system 80. The chassis 32 defines a front region 22, a back region 24, a crotch region 26 interconnecting the front and back regions, an inner surface 28 which is configured to contact the wearer, and an outer surface 30 opposite the inner surface which is configured to contact the wearer's clothing. As shown in further detail in FIGS. 2 and 3, the chassis 32 also defines a pair of transversely opposed side edges 36 and a pair of longitudinally opposed waist edges, which are designated front waist edge 38 and back waist edge 39. The front region 22 is contiguous with the front waist edge 38, and the back region 24 is contiguous with the back waist edge 39.

The illustrated chassis 32 includes a somewhat rectangular composite structure 33, a pair of transversely opposed front side panels 34, and a pair of transversely opposed back side panels 234. Alternatively, the absorbent composite can be shaped as, for example, an hourglass, or wider front and/or back sections. The composite structure 33 and side panels 34 and 234 may be integrally formed or may include two or more separate elements, as shown in FIGS. 2 and 3. The illustrated composite structure 33 includes an outer cover 40, a bodyside liner 42 which is connected to the outer cover in a superposed relation, and an absorbent pad 44 (FIG. 3) which is positioned or located between the outer cover 40 and the bodyside liner 42. The composite structure 33 may also include a pair of containment flaps 46, as shown in FIG. 3. A surge material may be positioned between the absorbent pad and body side liner 42. The absorbent composite structure 33 has opposite linear end edges 45 that form portions of the front and back waist edges 38 and 39, and opposite linear side edges 47 that form portions of the side edges 36 of the chassis 32 (FIGS. 2 and 3). For reference, arrows 48 and 49 depicting the orientation of the longitudinal axis and the transverse axis, respectively, of the training pant 20 are illustrated in FIGS. 2 and 3.

With the training pant 20 in the fastened position as partially illustrated in FIG. 1, the front and back regions 22 and 24 are joined together to define a three-dimensional pant configuration having a waist opening 50 and a pair of leg openings 52. The front region 22 includes the portion of the training pant 20 which, when worn, is positioned on the front of the wearer while the back region 24 includes the portion of the training pant which, when worn, is positioned on the back of the wearer. The crotch region 26 of the training pant 20 includes the portion of the training pant which, when worn, is positioned between the legs of the wearer and covers the lower torso of the wearer. The front and back side panels 34 and 234 include the portions of the training pant 20 which, when worn, are positioned on the hips of the wearer.

The front region 22 of the chassis 32 includes the transversely opposed front side panels 34 and a front center panel 35 (FIGS. 2 and 3) positioned between and interconnecting the side panels, along with a front waist elastic member 54 and any other connected components. The back region 24 of the chassis 32 includes the transversely opposed back side panels 234 and a back center panel 135 (FIGS. 2 and 3) positioned between and interconnecting the side panels, as well as a rear waist elastic member 56 and any other connected components. The waist edges 38 and 39 of the chassis 32 are configured to encircle the waist of the wearer when worn and provide the waist opening 50 which defines a waist perimeter dimension. Portions of the transversely opposed side edges 36 in the crotch region 26 generally define the leg openings 52.

The chassis 32 is configured to contain and/or absorb any body exudates discharged from the wearer. For example, the chassis 32 desirably, although not necessarily, includes the pair of containment flaps 46 which are configured to provide a barrier to the transverse flow of body exudates. A flap elastic member 53 (FIG. 3) is operatively joined with each containment flap 46 in any suitable manner as is well known in the art. The elasticized containment flaps 46 define an unattached edge which assumes an upright, generally perpendicular configuration in at least the crotch region 26 of the training pant 20 to form a seal against the wearer's body. The containment flaps 46 can be located along the transversely opposed side edges of the chassis 32, and can extend longitudinally along the entire length of the chassis or may only extend partially along the length of the chassis. Suitable constructions and arrangements for the containment flaps 46 are generally well known to those skilled in the art and are described in U.S. Pat. No. 4,704,116 issued Nov. 3, 1987 to Enloe, which is incorporated herein by reference.

To further enhance containment and/or absorption of body exudates, the training pant 20 desirably includes the front waist elastic member 54, the rear waist elastic member 56, and leg elastic members 58, as are known to those skilled in the art (FIG. 3). The waist elastic members 54 and 56 can be operatively joined to the outer cover 40 and/or bodyside liner 42 along the opposite waist edges 38 and 39, and can extend over part or all of the waist edges. The leg elastic members 58 are desirably operatively joined to the outer cover 40 and/or bodyside liner 42 along the opposite side edges 36 and positioned in the crotch region 26 of the training pant 20. The leg elastic members 58 are desirably longitudinally aligned along each side edge 47 of the composite structure 33. Each leg elastic member 58 has a front terminal point 63 and a back terminal point 65, which points represent the longitudinal ends of the elastic gathering caused by the leg elastic members. The front terminal points 63 are desirably located adjacent the longitudinally innermost parts of the front side panels 34, and the back terminal points 65 are desirably located adjacent the longitudinally innermost parts of the back side panels 234.

The flap elastic members 53, the waist elastic members 54 and 56, and the leg elastic members 58 can be formed of any suitable elastic material. As is well known to those skilled in the art, suitable elastic materials include sheets, strands or ribbons of natural rubber, synthetic rubber, or thermoplastic elastomeric polymers. The elastic materials can be stretched and adhered to a substrate, adhered to a gathered substrate, or adhered to a substrate and then elasticized or shrunk, for example with the application of heat; such that elastic constrictive forces are imparted to the substrate. In one particular embodiment, for example, the leg elastic members 58 include a plurality of dry-spun coalesced multifilament spandex elastomeric threads sold under the trade name LYCRA® and available from E. I. DuPont de Nemours and Company, Wilmington, Del., U.S.A.

The outer cover 40 desirably includes a material that is substantially liquid impermeable, and can be elastic, stretchable or nonstretchable. The outer cover 40 can be a single layer of liquid impermeable material, but desirably includes a multi-layered laminate structure in which at least one of the layers is liquid impermeable. For instance, the outer cover 40 can include a liquid permeable outer layer and a liquid impermeable inner layer that are suitably joined together by a laminate adhesive (not shown). Suitable laminate adhesives, which can be applied continuously or intermittently as beads, a spray, parallel swirls, or the like, can be obtained from Findley Adhesives, Inc., of Wauwatosa, Wis., U.S.A., or from National Starch and Chemical Company, Bridgewater, N.J., U.S.A. The liquid permeable outer layer can be any suitable material and desirably one that provides a generally cloth-like texture. One example of such a material is a 20 gsm (grams per square meter) spunbond polypropylene nonwoven web. The outer layer may also be made of those materials of which liquid permeable bodyside liner 42 is made. While it is not a necessity for the outer layer to be liquid permeable, it is desired that it provides a relatively cloth-like texture to the wearer.

The inner layer of the outer cover 40 can be both liquid and vapor impermeable, or can be liquid impermeable and vapor permeable. The inner layer is desirably manufactured from a thin plastic film, although other flexible liquid impermeable materials may also be used. The inner layer, or the liquid impermeable outer cover 40 when a single layer, prevents waste material from wetting articles, such as bedsheets and clothing, as well as the wearer and care giver. A suitable liquid impermeable film for use as a liquid impermeable inner layer, or a single layer liquid impermeable outer cover 40, is a 0.2 millimeter polyethylene film commercially available from Huntsman Packaging of Newport News, Va., U.S.A. If the outer cover 40 is a single layer of material, it can be embossed and/or matte finished to provide a more cloth-like appearance. As earlier mentioned, the liquid impermeable material can permit vapors to escape from the interior of the disposable absorbent article, while still preventing liquids from passing through the outer cover 40. A suitable "breathable" material is composed of a microporous polymer film or a nonwoven fabric that has been coated or otherwise treated to impart a desired level of liquid impermeability. A suitable microporous film is a PMP-1 film material commercially available from Mitsui Toatsu Chemicals, Inc., Tokyo, Japan, or an XKO-8044 polyolefin film commercially available from 3M Company, Minneapolis, Minn.

The liquid permeable bodyside liner 42 is illustrated as overlying the outer cover 40 and absorbent pad 44, and may but need not have the same dimensions as the outer cover 40. The bodyside liner 42 is desirably compliant, soft feeling, and non-irritating to the wearer's skin. Further, the bodyside liner 42 can be less hydrophilic than the absorbent pad 44, to present a relatively dry surface to the wearer and permit liquid to readily penetrate through its thickness.

The bodyside liner 42 can be manufactured from a wide selection of web materials, such as synthetic fibers (for example, polyester or polypropylene fibers), natural fibers (for example, wood or cotton fibers), a combination of natural and synthetic fibers, porous foams, reticulated foams, apertured plastic films, or the like. Various woven and nonwoven fabrics can be used for the bodyside liner 42. For example, the bodyside liner can be composed of a meltblown or spunbonded web of polyolefin fibers. The bodyside liner can also be a bonded-carded web composed of natural and/or synthetic fibers. The bodyside liner can be composed of a substantially hydrophobic material, and the hydrophobic material can, optionally, be treated with a surfactant or otherwise processed to impart a desired level of wettability and hydrophilicity. For example, the material can be surface treated with about 0.45 weight percent of a surfactant mixture including AHCOVEL® N-62 from Hodgson Textile Chemicals of Mount Holly, N.C., U.S.A. and GLUCOPON® 220UP from Henkel Corporation of Ambler, Pa., in an active ratio of 3:1. The surfactant can be applied by any conventional means, such as spraying, printing, brush coating or the like. The surfactant can be applied to the entire bodyside liner 42 or can be selectively applied to particular sections of the bodyside liner, such as the medial section along the longitudinal centerline.

A suitable liquid permeable bodyside liner 42 is a non-woven bicomponent web having a basis weight of about 27 gsm. The nonwoven bicomponent can be a spunbond bicomponent web, or a bonded carded bicomponent web. Suitable bicomponent staple fibers include a polyethylene/polypropylene bicomponent fiber available from CHISSO Corporation, Osaka, Japan. In this particular bicomponent fiber, the polypropylene forms the core and the polyethylene forms the sheath of the fiber. Other fiber orientations are possible, such as multi-lobe, side-by-side, end-to-end, or the like. While the outer cover 40 and bodyside liner 42 can include elastomeric materials, it can be desirable in some embodiments for the composite structure to be generally inelastic, where the outer cover, the bodyside liner and the absorbent pad include materials that are generally not elastomeric.

In accordance with one embodiment of this invention, the absorbent pad 44, as shown in FIG. 3, is positioned or located between the outer cover 40 and the bodyside liner 42, which components can be joined together by any suitable means, such as adhesives, as are well known in the art. The absorbent pad 44 is thin, flexible, and has a low mass, thus maximizing fit and comfort when dry, and resulting in some discomfort when wet. The term "low mass" refers to a total product weight of less than 30 grams or less than 25 grams or less than 20 grams for pants intended for use on children of 20 to 50 pounds.

The absorbent pad 44 suitably has a thickness of less than about 3 millimeters (mm), or less than about 1.5 mm, or, as another alternative, less than about 1 mm. The training pant 20 suitably has a combined thickness of all of its layers, including the outer cover 40, the absorbent pad 44, and the body side liner 42, of less than about 3 mm, or less than about 2.5 mm, or, alternatively, less than about 2 mm. The thickness of the absorbent pad 44 as well as the combined thickness of all layers, can be calculated according to the Bulk and Density Testing, described below.

Absorbent capacity of the absorbent article 20 is based on the anticipated insult volume of a single void. The absorbent capacity of the garment 20 can be adjusted to accommodate insults across a wide range of user positions, including standing, sitting and prone. For example, the capacity can be adjusted by zoning greater amounts of superabsorbent in certain areas of the pad 44 and lesser amounts of superabsorbent in other areas of the pad 44 and/or layering the superabsorbent, and/or using different types of superabsorbent in different locations in the absorbent structure.

The absorbent capacity, as determined by 0.5 psi saturation capacity, is approximately 90-150% of the anticipated single void volume, or no more than three times the anticipated insult size, or no more than twice the anticipated single void volume. For example, absorbent articles 20 can be designed and produced to accommodate children between about 18 months and about 60 months old, with insult volumes from 30 ml to 180 ml, or from less than 50 ml to 150 ml, and higher if necessary. Anticipated single void insult size is typically less than 60 ml but can be greater than 100 ml.

The overall absorbent capacity of the absorbent pad 44 is expressed in terms of grams (g) of fluid absorbed (and retained). The overall absorbent capacity of the absorbent pad 44 is suitably not greater than about three times an anticipated insult volume, or not greater than about two times an anticipated insult volume, and thus is desirably capable of accommodating an insult having a volume of about 30 grams (g) to about 400 g, or desirably about 40 g to about 300 g, or about 50 g to about 150 g. The saturated capacity (i.e. absorbent efficiency) of the absorbent pad 44 is expressed in terms of grams (g) of fluid retained per gram (g) of absorbent structure, wherein a higher value represents a greater efficiency. The saturated capacity of the absorbent pad 44 is suitably greater than about 7 g/g, or about 9 g/g to about 11 g/g, or, alternatively, greater than about 12.0 g/g. Both overall absorbent capacity and saturated capacity of the absorbent pad 44 are determined by a saturated capacity test, described below.

This absorbent article capacity and product design provides better leakage performance than cloth training pants or underwear, with low leakage probabilities for insults below the anticipated single void volume. When leaks do occur, the severity of the leak is kept at a manageable level. For example, the absorbent article may experience less than 15%, or less than 10%, of insult liquid volume runoff when the product is insulted with volumes up to the target void volume, or anticipated insult volume, in a Single Insult Test, described below. Leakage performance of the product is enhanced by the containment flaps 46 and the leg elastics 58 which are removed for the Single Insult Test.

An absorbent pad 44 including a fluff pulp and superabsorbent material, for example, possibly in combination with other components, is able to retain a specific amount of fluid that is determined by the individual fluid capacities of the components and their relative percentages within the absorbent structure 44. The superabsorbent material, or superabsorbent polymer (SAP), is highly efficient, whereas the fluff pulp material is moderately efficient. Synthetic fibers, such as polyester fibers, are generally very inefficient. An "efficient" absorbent structure will retain a relatively large volume of fluid, whereas an "inefficient" absorbent structure will retain a relatively small volume of fluid.

The absorbent pad 44 can be any structure which is generally compressible, conformable, non-irritating to the wearer's skin, and capable of absorbing and retaining liquids and certain body wastes at the levels discussed herein. The absorbent pad 44 can be manufactured in a wide variety of sizes and shapes, and from a wide variety of liquid absorbent materials commonly used in the art. For example, the absorbent pad 44 can suitably include a matrix of hydrophilic fibers, such as a web of cellulosic fluff, mixed with particles of a high-absorbency material commonly known as superabsorbent material. In a particular embodiment, the absorbent pad 44 includes a matrix of cellulosic fluff, such as wood pulp fluff, and superabsorbent hydrogel-forming particles. The wood pulp fluff can be exchanged with synthetic, polymeric, meltblown fibers or with a combination of meltblown fibers and natural fibers. The superabsorbent particles can be substantially homogeneously mixed with the hydrophilic fibers or can be nonuniformly mixed. The fluff and superabsorbent particles can also be selectively placed into desired zones of the absorbent pad 44 to better contain and absorb body exudates. The concentration of the superabsorbent particles can also vary through the thickness of the absorbent pad 44. Alternatively, the absorbent pad 44 can include a laminate of fibrous webs and superabsorbent material or other suitable means of maintaining a superabsorbent material in a localized area.

Suitable superabsorbent materials can be selected from natural, synthetic, and modified natural polymers and materials. The superabsorbent materials can be inorganic materials, such as silica gels, or organic compounds, such as crosslinked polymers. Suitable superabsorbent materials are available from various commercial vendors, such as Dow Chemical Company located in Midland, Mich., U.S.A., and Stockhausen GmbH & Co. KG, D-47805 Krefeld, Federal Republic of Germany. Typically, a superabsorbent material is capable of absorbing at least about 15 times its weight in water, and desirably is capable of absorbing more than about 25 times its weight in water.

More particularly, the absorbent pad 44 can include an extremely thin absorbent composite material sold under the trade name NOVATHIN® available from EAM Corporation located in Jessup, Ga., U.S.A., and/or an ultra-thin-absorbent (UTA) material including a mixture of SAP and pulp fiber. An example of a suitable UTA may include 3.7 grams (g) of FAVOR® SXM 9543 SAP, available from Stockhausen GmbH & Co. KG located in Krefeld, Fed. Rep. of Germany, and 3.7 g of NB416 pulp fiber available from Weyerhauser located in Federal Way, Wash.

In one embodiment, the absorbent pad 44 can be generally rectangular in shape, and can include a blend of wood pulp fluff and superabsorbent material. One preferred type of fluff is identified with the trade designation CR1654, available from U.S. Alliance, Childersburg, Ala., U.S.A., and is a bleached, highly absorbent sulfate wood pulp containing primarily soft wood fibers. As a general rule, the superabsorbent material is present in the absorbent pad 44 in an amount of from about 5 to about 90 weight percent based on total weight of the absorbent pad 44. The absorbent pad 44 suitably has a density within the range of about 0.10 to about 0.50 grams per cubic centimeter. The absorbent pad 44 may or may not be wrapped or encompassed by a suitable tissue wrap that maintains the integrity and/or shape of the absorbent pad 44.

The chassis 32 can also incorporate other materials that are designed primarily to receive, temporarily store, and/or transport liquid along the mutually facing surface with the absorbent pad 44, thereby maximizing the overall absorbent capacity of the absorbent pad 44, if desired. One suitable material is referred to as a surge layer (not shown) and includes a material having a basis weight of about 50 to about 120 grams per square meter (gsm), and including a through-air-bonded-carded web of a homogenous blend of 60 percent 3 denier type T-256 bicomponent fiber including a polyester core/polyethylene sheath and 40 percent 6 denier type T-295 polyester fiber, both commercially available from Kosa Corporation of Salisbury, N.C., U.S.A. Another example of a suitable surge layer may include a material made of 6 denier polyethylene terephthalate (PET) and 6 denier bicomponent binder fiber, having a basis weight of about 50 to about 120 gsm.

As noted previously, the illustrated training pant 20 has front and back side panels 34 and 234 disposed on each side of the chassis 32. These transversely opposed front side panels 34 and transversely opposed back side panels 234 can be permanently bonded to the composite structure 33 of the chassis 32 in the respective front and back regions 22 and 24, and can be releasably attached to one another by a fastening system 80. Alternatively, instead of being releasably attachable, the front and back side panels 34, 234 can be permanently bonded to one another, respectively, to create a pull-on pant.

As shown best in FIGS. 2 and 3, the front side panels 34 can be permanently bonded to and extend transversely beyond the linear side edges 47 of the composite structure 33 in the front region 22 along attachment lines 66, and the back side panels 234 can be permanently bonded to and extend transversely beyond the linear side edges of the composite structure in the back region 24 along attachment lines 66. The side panels 34 and 234 may be attached using attachment means known to those skilled in the art such as adhesive, thermal or ultrasonic bonding. The side panels 34 and 234 can also be formed as a portion of a component of the composite structure 33, such as the outer cover 40 or the bodyside liner 42.

In particular embodiments for improved fit and appearance, the side panels 34 and 234 desirably have an average length dimension measured parallel to the longitudinal axis 48 that is about 20 percent or greater, and particularly about 25 percent or greater, of the overall length dimension of the absorbent article, also measured parallel to the longitudinal axis 48. For example, in training pants having an overall length dimension of about 54 centimeters, the side panels 34 and 234 desirably have an average length dimension of about 10 centimeters or greater, such as about 15 centimeters. While each of the side panels 34 and 234 extend from the waist opening 50 to one of the leg openings 52, the back side panels 234 have a continually decreasing length dimension moving from the attachment line 66 to a distal edge 68b of the back panel 234, as is best shown in FIGS. 2 and 3.

Each of the side panels 34 and 234 can include one or more individual, distinct pieces of material. In particular embodiments, for example, each side panel 34 and 234 can include first and second side panel portions that are joined at a seam, with at least one of the portions including an elastomeric material. Still alternatively, each individual side panel 34 and 234 can include a single piece of material which is folded over upon itself along an intermediate fold line (not shown).

The side panels 34 and 234 desirably include an elastic material capable of stretching in a direction generally parallel to the transverse axis 49 of the training pant 20. In particular embodiments, the front and back side panels 34 and 234 may each include an interior portion 78 disposed between the distal edge 68a, 68b and the respective front or back center panel 35 or 135. In the illustrated embodiment in FIG. 3, the interior portions 78 are disposed between the distal edges 68a, 68b and the side edges 47 of the rectangular composite structure 33. The elastic material of the side panels 34 and 234 can be disposed in the interior portions 78 to render the side panels elastomeric in a direction generally parallel to the transverse axis 49. Most desirably, each side panel 34 and 234 is elastomeric from a waist end edge 72 to a leg end edge 70. More specifically, individual samples of side panel material, taken between the waist end edge 72 and the leg end edge 70 parallel to the transverse axis 49 and having a length from the attachment line 66 to the distal edge 68a, 68b and a width of about 2 centimeters, are all elastomeric.

Suitable elastic materials, as well as one described process of incorporating elastic side panels into a training pant, are described in the following U.S. Pat. No. 4,940,464 issued Jul. 10, 1990 to Van Gompel et al.; U.S. Pat. No. 5,224,405 issued Jul. 6, 1993 to Pohjola; U.S. Pat. No. 5,104,116 issued Apr. 14, 1992 to Pohjola; and U.S. Pat. No. 5,046,272 issued Sep. 10, 1991 to Vogt et al.; all of which are incorporated herein by reference. In particular embodiments, the elastic material includes a stretch-thermal laminate (STL), a neck-bonded laminated (NBL), a reversibly necked laminate, or a stretch-bonded laminate (SBL) material. Methods of making such materials are well known to those skilled in the art and described in U.S. Pat. No. 4,663,220 issued May 5, 1987 to Wisneski et al.; U.S. Pat. No. 5,226,992 issued Jul. 13, 1993 to Morman; and European Patent Application No. EP 0 217 032 published on Apr. 8, 1987 in the names of Taylor et al., all of which are incorporated herein by reference. Alternatively, the side panel material may include other woven or nonwoven materials, such as those described above as being suitable for the outer cover 40 or bodyside liner 42, or stretchable but inelastic materials.

As mentioned, the training pant 20 according to the present invention may include a fastening system 80 for securing the training pant about the waist of the wearer (FIG. 1). The illustrated fastening system 80 may include fastening components 82 that are adapted to refastenably connect to mating fastening components 84. In one embodiment, one surface of each of the fastening components 82 and 84 includes a plurality of engaging elements that project from that surface. The engaging elements of these fastening components 82 are adapted to repeatedly engage and disengage the engaging elements of the mating fastening components 84.

In one particular embodiment, the fastening components 82 each include hook type fasteners and the mating fastening components 84 each include complementary loop type fasteners. In another particular embodiment, the fastening components 82 each include loop type fasteners and the mating fastening components 84 each include complementary hook type fasteners. The fastening components 82 and the mating fastening components 84 are desirably rectangular, although they may alternatively be square, round, oval, curved or otherwise non-rectangularly shaped.

Loop type fasteners typically include a fabric or material having a base or backing structure and a plurality of loop members extending upwardly from at least one surface of the backing structure. The loop material can be formed of any suitable material, such as acrylic, nylon or polyester, and can be formed by methods such as warp knitting, stitch bonding or needle punching. Suitable loop materials are available from Guilford Mills, Inc., Greensboro, N.C., U.S.A. under the trade designation No. 36549.

Hook type fasteners typically include a fabric or material having a base or backing structure and a plurality of hook members extending upwardly from at least one surface of the backing structure. In contrast to the loop type fasteners which desirably include a flexible fabric, the hook material advantageously includes a resilient material to minimize unintentional disengagement of the fastener components as a result of the hook material becoming deformed and catching on clothing or other items. The term "resilient" as used herein refers to an interlocking material having a predetermined shape and the property of the interlocking material to resume the predetermined shape after being engaged and disengaged from a mating, complementary interlocking material. Suitable hook material can be molded or extruded of nylon, polypropylene or another suitable material. Suitable single-sided hook materials for the fastening components 82 or the mating fastening components 84 are available from Velcro Industries B.V., Amsterdam, Netherlands or affiliates thereof, and are identified as Velcro HTH-829 with a uni-directional hook pattern and having a thickness of about 0.089 millimeters (3.5 mils) and HTH-851 with a uni-directional hook pattern and having a thickness of about 0.051 millimeters (2 mils).

As described herein, the various components of the absorbent garment 20 can be integrally assembled together employing various types of suitable attachment means, such as adhesive, sonic and thermal bonds or combinations thereof. The resulting product is an absorbent article having cloth-like thinness, low absorbent capacity, and which also provides leakage protection.

EXAMPLES

Example 1

One example of a prototype product designed to handle a single void volume of 100 cc at a flow rate of 15 cc/sec while a wearer is in a standing position includes 5.2 g of a 3000255 EAM NOVATHIN® composite with a 0.5 psi saturation capacity of 23 g/g. The EAM composite is placed in the target zone, i.e., crotch area, of a training pant prototype based on or similar to a PULL-UPS® Training Pant with the absorbent removed and a different absorbent in its place. A high intake surge, 50 gsm 6 denier PET/3 denier bicomponent binder fiber is placed over the composite in the target zone. A caliper (in the front) of the finished product under 0.2 psi load is about 2 mm. The pant is constructed and sized to take advantage of the low mass, thin absorbent.

Example 2

A single-insult prototype pant was produced having an absorbent system including a 102 mm by 385 mm piece of 2000155 EAM NOVATHIN® absorbent composite with a 50 gsm 6 denier polyethylene terephthalate (PET)/3 denier bicomponent binder fiber surge placed over the composite in the target zone and a 0.5 osy spunbond liner also placed over the composite. Full product thickness was 2.5 mm. This product had a 0.5 psi saturation capacity of 150 ml. The occurrence of runoff in this product was assessed with a Single Insult test, described in detail below, using 60, 80 and 100 ml of 0.9% NaCl saline at 5 ml/sec. The flaps and leg elastics were removed in this static cradle test. Results are shown in Table 1. When insulted with 60 ml of physiological saline there was no runoff. Runoff increases with insult volume, as shown.

TABLE 1

Single Insult Test of Example 3 Insulted with 0.9% NaCl Saline

| Saline (ml) | Sample | Dry Weight (g) | Bulk (mm) | Runoff (g) |
|---|---|---|---|---|
| 60 | 1 | 21.63 | 2.43 | None |
|  | 2 | 21.71 | 2.60 | None |
|  | 3 | 21.58 | 2.44 | None |
|  | 4 | 21.51 | 2.40 | None |
|  | 5 | 21.28 | 2.35 | None |
|  | Average | 21.54 | 2.44 | None |
| 80 | 1 | 22.02 | 2.59 | None |
|  | 2 | 21.96 | 2.36 | 10.64 |
|  | 3 | 21.71 | 2.43 | 5.35 |
|  | 4 | 21.92 | 2.54 | None |
|  | 5 | 22.03 | 2.51 | None |
|  | Average | 21.93 | 2.49 | N/A |
| 100 | 1 | 22.07 | 2.47 | 21.08 |
|  | 2 | 21.95 | 2.42 | 7.42 |
|  | 3 | 21.01 | 2.44 | 15.52 |
|  | 4 | 21.31 | 2.51 | 19.23 |
|  | 5 | 21.95 | 2.33 | 7.68 |
|  | Average | 21.66 | 2.43 | 14.19 |

The prototype pant product with the EAM NOVATHIN® absorbent composite showed excellent leakage protection performance, with no runoff in the Single Insult Test with 60 ml insults. Anticipated single void insult size is typically less than 60 ml but greater than 100 ml. The prototype pants showed good protection at higher insult volumes with runoff values of less than 8 ml for 80 ml insults and less than 15 ml for 100 ml insults. Leakage performance of the product is benefitted from leg flaps and leg elastics which were removed for the Single Insult testing.

Example 3

A single-insult prototype pant was produced with a 102 mm by 385 mm piece of an online UTA targeting a 0.5 psi saturation capacity of 150 ml. The online UTA contained 3.7 g of FAVOR® SXM 9543 SAP and 3.7 g of NB416 pulp fiber. The UTA pad was 100 mm by 385 mm and approximately 0.8 mm thick. This absorbent pad was incorporated into a PULL-UPS® Training Pant in place of the existing absorbent pad. Full product thickness was 2.8 mm. The occurrence of runoff in this product was assessed with a Single Insult Test, described in detail below, using 60, 80 and 100 ml of 0.9% NaCl saline at 5 ml/sec. The flaps and leg elastics were removed in this static cradle test. Results are shown in Table 2. As in the previous example, when insulted with 60 ml of physiological saline there was no runoff. Runoff increases with insult volume, as shown.

TABLE 2

Single Insult Test of Example 3 Insulted with 0.9% NaCl Saline

| Saline (ml) | Sample | Dry Weight (g) | Bulk (mm) | Runoff (g) |
|---|---|---|---|---|
| 60 | 1 | 22.75 | 2.86 | None |
|  | 2 | 23.49 | 2.78 | None |
|  | 3 | 22.60 | 2.85 | None |
|  | 4 | 22.99 | 2.70 | None |
|  | 5 | 23.02 | 2.60 | None |
|  | Average | 22.97 | 2.76 | None |
| 80 | 1 | 22.57 | 3.02 | 2.87 |
|  | 2 | 21.94 | 2.96 | None |
|  | 3 | 22.17 | 2.82 | 5.40 |
|  | 4 | 22.93 | 2.71 | None |
|  | 5 | 22.89 | 2.67 | None |
|  | Average | 22.50 | 2.84 | N/A |
| 100 | 1 | 23.27 | 2.68 | 11.74 |
|  | 2 | 22.71 | 2.63 | 12.40 |
|  | 3 | 23.36 | 2.64 | 2.24 |
|  | 4 | 22.44 | 2.72 | 12.12 |
|  | 5 | 23.09 | 2.78 | None |
|  | Average | 22.97 | 2.69 | 9.63 |

The prototype pant product with the UTA absorbent composite showed excellent leakage protection performance, with no runoff in the Single Insult Test with 60 ml insults. Anticipated single void insult size is typically less than 60 ml but can be greater than 100 ml. The prototype pants showed good protection at higher insult volumes with runoff values of less than 8 ml for 80 ml insults and less than 15 ml for 100 ml insults. Leakage performance of the product is benefitted from leg flaps and leg elastics which were removed for the Single Insult testing.

Example 4

In this example, prototype pants with UTA absorbent composite were produced at a superabsorbent polymer (SAP) level of 60%. Humidified air was pulled through the absorbent composite and the absorbent composite was debulked with heat to reduce stiffness.

Microperforated flat screens having perforations of less than 400 microns equivalent diameter were used during the formation of the absorbent composite. The contour segments were straight (rectangular pads versus shaped pads). The microperforated screens were able to prevent SAP from entering the drum interior to produce consistent absorbent weights, even at SAP levels approaching 60%. On the macro scale, airflow uniformity and volume were maintained at an adequate level for good pad formation.

Adding small amounts of moisture to the absorbent was desired as a means of reducing the debulking pressure required to achieve the target densities (>0.3 g/cc) of the UTA absorbent. Humidified air was drawn through the pad to provide a more uniform distribution of moisture through the thickness of the absorbent. A heating element and blower motor were used to pipe hot air to a hood installed over a vacuum conveyor between the forming drum and a pre-debulker. Filtered tap water was merged with compressed air (20 psi) and introduced into the warm air stream as a fine mist via an atomizing spray nozzle with a 0.028-inch opening. A maximum humidity of approximately 40% relative humidity (RH) at an air temperature of 120 degrees Celsius was achieved in the air stream before moisture collected within the duct work. Once the best moisture conditions were achieved, absorbent pads were produced. Approximately 1% of moisture was added to the pads via this technique. Humidification permitted opening the compaction roll 5 mils while achieving the same absorbent pad caliper as was obtainable for a dry pad.

Round, uniform thickness shells were installed on the debulker to produce an even caliper across the length of the flat-screen UTA absorbents. The pad dimensions for the UTA pads were approximately 390 mm×95 mm. Table 3 describes the samples of absorbents that were collected. Saturated capacity was calculated using the procedure described in detail below. All UTA samples were produced with FAVOR® SXM 9543 SAP. Sample 1 was produced with Stockhausen FAVOR® SXM 880 superabsorbent using forming screens that are used by Kimberly-Clark Corporation to make PULL-UPS® Training Pants.

TABLE 3

Properties of Manufactured UTA Absorbent Composites

| Sample | Basis Weight (gsm) | SAP (%) | Pulp | SAP Weight (g) | Pulp Weight (g) | Saturated Capacity (g) | Bulk (mm) | Density (g/cc) |
|---|---|---|---|---|---|---|---|---|
| 1 |  | 44 | CR1654 | 11 | 14 | 475 | 5 | 0.2 |
| 2 | 670 | 60 | NB416 | 14.8 | 9.9 | 450 | 1.8 | 0.37 |
| 3 | 670 | 60 | NB416 | 14.8 | 9.9 | 450 | 1.8 | 0.37 |
| 4 | 510 | 60 | NB416 | 11.3 | 7.5 | 350 | 1.4 | 0.36 |
| 5 | 260 | 30 | NB416 | 2.9 | 6.7 | 125 | 0.7 | 0.37 |
| 6 | 200 | 50 | NB416 | 3.7 | 3.7 | 125 | 0.6 | 0.33 |
| 7 | 670 | 60 | NB416 | 14.8 | 9.9 | 450 | 1.8 | 0.37 |

Single Insult Test Method

Figure 4:
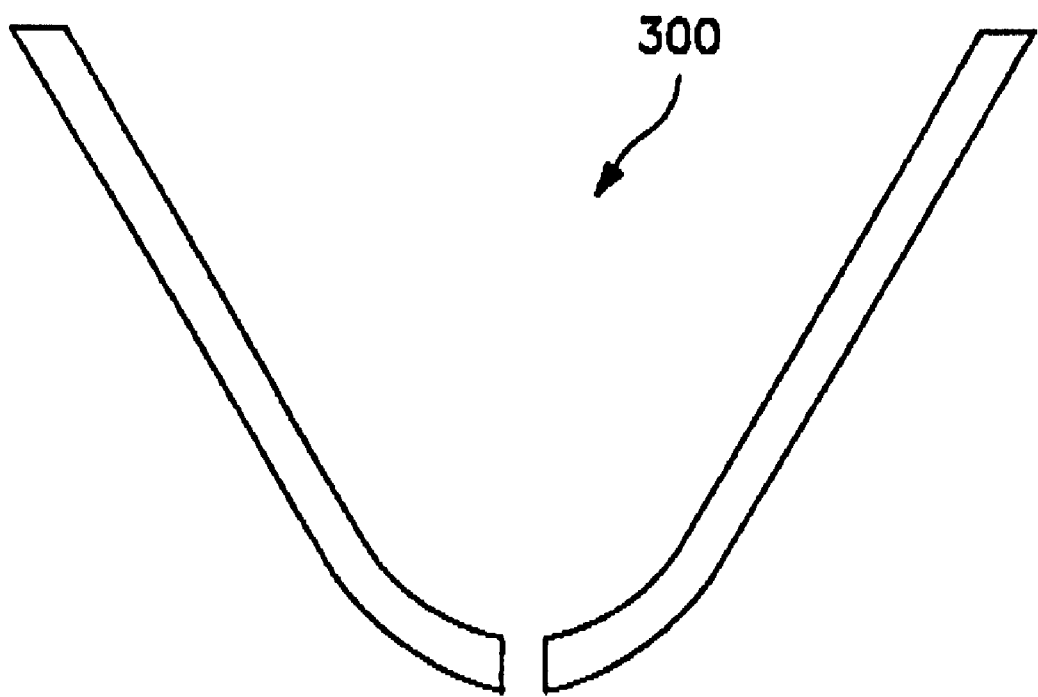
FIG. 4 representatively shows a cradle suitable for use in a Single Insult Test.

In this test, an absorbent material is placed in an acrylic cradle to simulate body curvature of a wearer. Such a cradle is illustrated in FIG. 4. The cradle has a width into the page of the drawing as shown of 33 centimeters (cm) and the ends are blocked off. The cradle has a height of 19 cm, an inner distance between the upper arms of 30.5 cm, and an angle between the upper arms of 60 degrees. The cradle has a 6.5 millimeter wide slot at the lowest point, which runs the length of the cradle into the page. The test is designed to determine how quickly an absorbent material is able to absorb an insult as opposed to allowing the insulting fluid to run off the sample without being absorbed.

The material to be tested is weighed. The thickness of the material in the insult area is determined as described below under Bulk and Density Testing. The insult point is marked at 5.5 inches from the front of the absorbent composite, and the center of the absorbent composite is marked. Materials are placed in the cradle, with the center of the absorbent composite at the bottom slot of the cradle. A plastic capture container of known weight is placed under the cradle. The material is insulted with the appropriate volume of 0.9 w/v % saline solution at a rate of about 5 milliliters/second. The nozzle of the saline delivery pump is held about 0.5 cm away from the surface of the absorbent composite and with the orifice normal to the absorbent composite surface, at the marked insult point. Following delivery of the insult, the mass of any runoff fluid in the capture container is determined and recorded. Any runoff that does not land in the capture container is wiped up with a weighed paper towel, after which the wet towel is again weighed. The mass difference between the towel in wet and dry states is added to the runoff mass in the container and this total mass is recorded as the runoff mass.

Bulk and Density Testing

A region of the absorbent pad to be tested is placed under a 0.2 psi weight, and the bulk of the absorbent in this region is recorded. The area under compression should be larger than a 2-inch by 2-inch (5.08-cm by 5.08-cm) square. A suitable tester for absorbent bulk is a Starret-type bulk tester equipped with a 3-inch diameter brass foot that applies a weight of 0.2 psi. The area under compression is marked around the perimeter of the weight while the weight is in place. The weight is removed, and a 2-inch by 2-inch square is cut out from within the outlined region, such as by a die cut. Any tissue present on the absorbent pad is removed, and the square is weighed. The density is determined by the following calculation: density =(mass of absorbent in grams)/[(5.08 cm)$^2$×(bulk in cm)].

Edge-Wise Compression Test

The method by which the Edge-wise Compression (EC) value can be determined is set forth below.

A 2-inch by 12-inch (5.1-cm×30.5-cm) piece of absorbent material is cut with its longer dimension aligned with the longitudinal direction of the product or raw material web. The weight of the sample is determined. The thickness of the material is determined under a 0.2 psi (1.38 kPa) load. The material is formed into a cylinder having a height of 2 inches (5.1 cm), and with the two ends having 0-0.125 inch (0-3.18 mm) overlap, the material is stapled together with three staples. One staple is near the middle of the width of the product, the other two nearer each edge of the width of the material. The longest dimension of the staple is in the circumference of the formed cylinder to minimize the effect of the staples on the testing.

An INSTRON tester, or similar instrument, is configured with a bottom platform, a platen larger than the circumference of the sample to be tested and parallel to the bottom platform, attached to a compression load cell placed in the inverted position. The specimen is placed on the platform, under the platen. The platen is brought into contact with the specimen and compresses the sample at a rate of 25 mm/min. The maximum force obtained in compressing the sample to 50% of its width (1 inch) (2.54 cm) is recorded.

If the material buckles, it is typical for the maximum force to be reached before the sample is compressed to 50%. In a product where the length of the absorbent is less than 12 inches (30.5 cm), the EC value of the material can be determined in the following manner. A detailed discussion of the edge-wise compression strength has been given in The Handbook Of Physical And Mechanical Testing Of Paper And Paperboard, Richard E. Mark editor, Dekker 1983, (Vol. 1). Based on theoretical models governing buckling stresses, in the Edge-wise Compression configuration described, the buckling stress is proportional to $E*t(H')$ with the proportionality constant being a function of $H2/(R*t)$ where E is the elastic modulus, H is the height of the cylinder, R is the radius of the cylinder, and t is the thickness of the material. Expressing the stress in terms of force per basis weight, it can be shown that the parameter that needs to be maintained constant is H2/R. Therefore, for a sample that is smaller than 12 inches (30.5 cm), the largest possible circle should be constructed and its height (width of the sample being cut out) adjusted such that H2/R equals 2.1 inches (5.3 cm).

Modified Saturated Capacity Test Method

Figure 5:
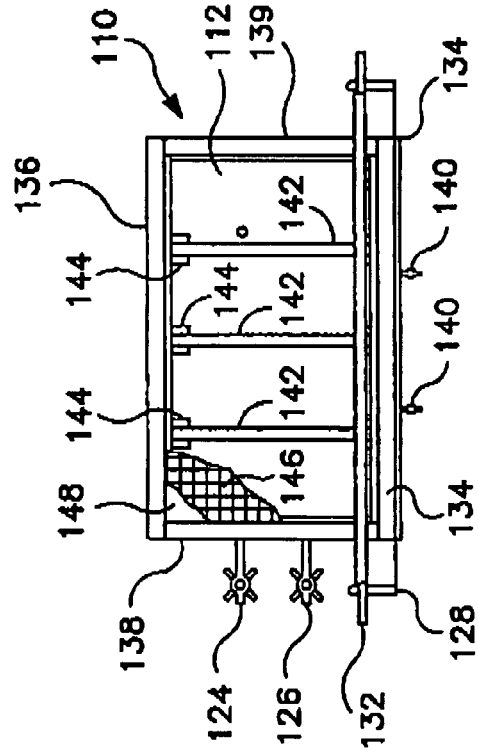
FIG. 5 representatively shows a partially cut away top view of a saturated capacity tester.
Figure 7:
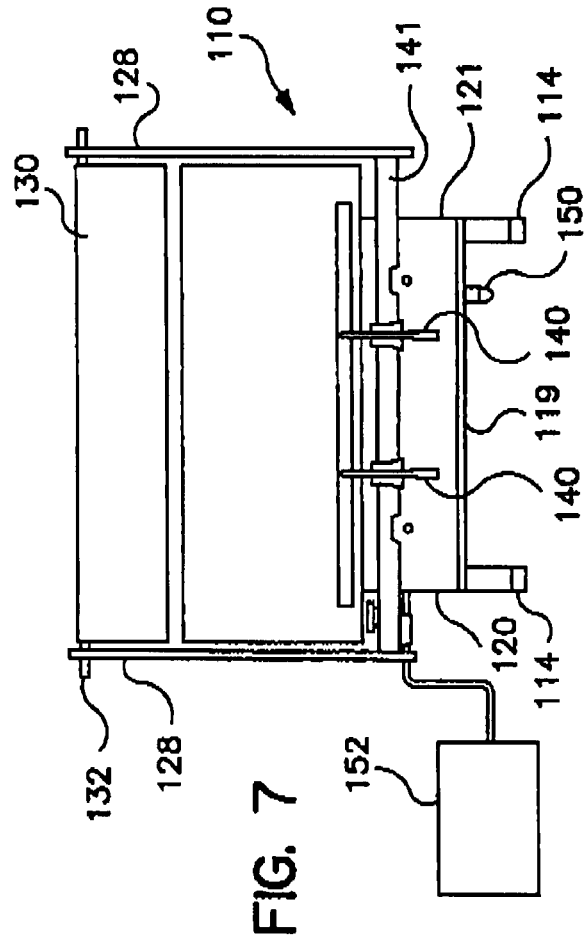
FIG. 7 representatively shows a rear view of a saturated capacity tester.
Figure 6:
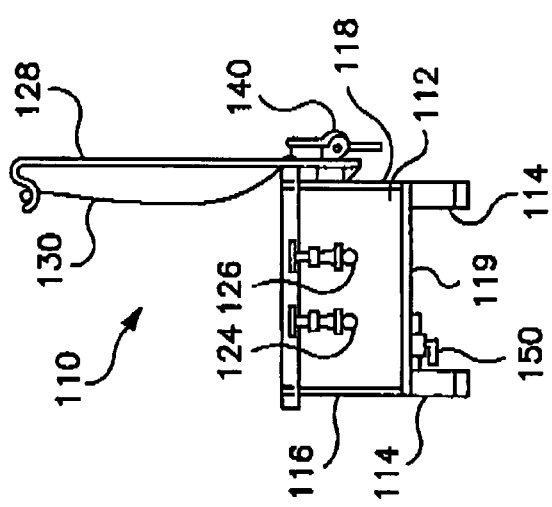
FIG. 6 representatively shows a side view of a saturated capacity tester.

Saturated Capacity is determined using a Saturated Capacity (SAT CAP) tester with a Magnahelic vacuum gage and a latex dam. Referring to FIGS. 5-7, a Saturated Capacity tester vacuum apparatus 110 comprises a vacuum chamber 112 supported on four leg members 114. The vacuum chamber 112 includes a front wall member 116, a rear wall member 118 and two side walls 120 and 121. The wall members are about 0.5 inch thick, and are constructed and arranged to provide a chamber having outside dimensions measuring 23.5 inches in length, 14 inches in width and 8 inches in depth.

A vacuum pump (not shown) operably connects with the vacuum chamber 112 through an appropriate vacuum line conduit and a vacuum valve 124. In addition, a suitable air bleed line connects into the vacuum chamber 112 through an air bleed valve 126. A hanger assembly 128 is suitably mounted on the rear wall 118 and is configured with S-curved ends to provide a convenient resting place for supporting a latex dam sheet 130 in a convenient position away from the top of the vacuum apparatus 110. A suitable hanger assembly can be constructed from 0.25 inch diameter stainless steel rod. The latex sheet 130 is looped around a dowel member 132 to facilitate grasping and to allow a convenient movement and positioning of the latex sheet 130. In the illustrated position, the dowel member 132 is shown supported in a hanger assembly 128 to position the latex sheet 130 in an open position away from the top of the vacuum chamber 112.

A bottom edge of the latex sheet 130 is clamped against a rear edge support member 134 with suitable securing means, such as toggle clamps 140. The toggle clamps are mounted on the rear wall member 118 with suitable spacers 141 which provide an appropriate orientation and alignment of the toggle clamps 140 for the desired operation. Three support shafts 142 are 0.75 inches in diameter and are removably mounted within the vacuum chamber 112 by means of support brackets 144. The support brackets 144 are generally equally spaced along the front wall member 116 and the rear wall member 118 and arranged in cooperating pairs. In addition, the support brackets 144 are constructed and arranged to suitably position the uppermost portions of the support shafts 142 flush with the top of the front, rear and side wall members of the vacuum chamber 112. Thus, the support shafts 142 are positioned substantially parallel with one another and are generally aligned with the side wall members 120 and 121. In addition to the rear edge support member 134, the apparatus 110 includes a front support member 136 and two side support members 138 and 139. Each side support member measures about 1 inch in width and about 1.25 inches in height. The lengths of the support members are constructed to suitably surround the periphery of the open top edges of the vacuum chamber 112, and are positioned to protrude above the top edges of the chamber wall members by a distance of about 0.5 inches.

A layer of egg crating type material 146 is positioned on top of the support shafts 142 and the top edges of the wall members of the vacuum chamber 112. The egg crate material extends over a generally rectangular area measuring 23.5 inches by 14 inches, and has a depth measurement of about 0.38 inches. The individual cells of the egg crating structure measure about 0.5 inch square, and the thin sheet material comprising the egg crating is composed of a suitable material, such as polystyrene. For example, the egg crating material can be McMaster Supply Catalog No. 162 4K 14, translucent diffuser panel material. A layer of 0.19 mesh nylon screening 148, which measures 23.5 inches by 14 inches, is placed on top of egg crating material 146.

A suitable drain line and a drain valve 150 connect to bottom plate member 119 of the vacuum chamber 112 to provide a convenient mechanism for draining liquids from the vacuum chamber 112. The various wall members and support members of tester apparatus 110 may be composed of a suitable noncorroding, moisture-resistant material, such as polycarbonate plastic. The various assembly joints may be affixed by solvent welding, and the finished assembly of the tester is constructed to be watertight. A vacuum gauge 152 operably connects through a conduit into the vacuum chamber 112. A suitable pressure gauge is a Magnahelic differential gauge capable of measuring a vacuum of 0-100 inches of water, such as a No. 2100 gauge available from Dwyer Instrument Incorporated.

The dry product or other absorbent structure is weighed and then placed in excess 0.9% saline solution and allowed to soak for 20 minutes. After the 20 minute soak time, the absorbent structure is placed on the egg crate material and mesh nylon screening of the Saturated Capacity tester. The latex sheet is placed over the absorbent structure(s) and the entire egg crate grid so that the latex sheet creates a seal when a vacuum is drawn on the tester. A vacuum of 0.5 pounds per square inch (psi) is held in the Saturated Capacity tester for five minutes. The vacuum creates a pressure on the absorbent structure(s), causing drainage of some liquid. After five minutes at 0.5 psi vacuum, the latex sheet is rolled back and the absorbent structure(s) are weighed to generate a wet weight.

The overall capacity of each absorbent structure is determined by subtracting the dry weight of each absorbent from the wet weight of that absorbent determined at this point in the procedure. The 0.5 psi SAT CAP or SAT CAP of the absorbent structure is determined by the following formula:

$$SAT\ CAP = (wet\ weight - dry\ weight)/dry\ weight;$$

wherein the SAT CAP value has units of grams fluid/gram absorbent. For both overall capacity and SAT CAP, a minimum of four specimens of each sample should be tested and the results averaged. If the absorbent structure has low integrity or disintegrates during the soak or transfer procedures, the absorbent structure can be wrapped in a containment material such as paper toweling, for example Hi-Dri® paper towels manufactured by Kimberly-Clark Corporation, Neenah, Wis., U.S.A. The absorbent structure can be tested with the overwrap in place and the capacity of the overwrap can be independently determined and subtracted from the wet weight of the total wrapped absorbent structure to obtain a wet absorbent weight.

It will be appreciated that details of the foregoing embodiments, given for purposes of illustration, are not to be construed as limiting the scope of this invention. Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention, which is defined in the following claims and all equivalents thereto. Further, it is recognized that many embodiments may be conceived that do not achieve all of the advantages of some embodiments, particularly of the preferred embodiments, yet the absence of a particular advantage shall not be construed to necessarily mean that such an embodiment is outside the scope of the present invention.

What is claim is:

1. A disposable absorbent article comprising:
   an outer cover;
   a body side liner at least partially bonded to the outer cover; and
   an absorbent pad positioned between the outer cover and the body side liner, the absorbent pad having a thickness of less than about 2 millimeters;
   the outer cover, the body side liner, the absorbent pad, and any additional layers between the outer cover and the body side liner, having a combined thickness of less than about 3 millimeters; and
   the disposable absorbent article having an absorbent capacity of less than three times an anticipated single insult volume, wherein the disposable absorbent article provides less than 15% insult liquid volume runoff when the article is insulted with the anticipated single insult volume.

2. The absorbent article of claim 1, wherein the absorbent pad comprises superabsorbent and fluff pulp.

3. The absorbent article of claim 1, wherein the absorbent pad comprises multiple layers of superabsorbent.

4. The absorbent article of claim 1, wherein the absorbent pad comprises at least two different superabsorbent materials and each of the superabsorbent materials is located in a different location within the absorbent pad.

5. The absorbent article of claim 1, wherein the absorbent pad comprises a greater amount of superabsorbent in a first region of the absorbent pad and a lesser amount of superabsorbent in a second region of the absorbent pad.

6. The absorbent article of claim 1, further comprising a surge layer between the absorbent pad and the body side liner.

7. The absorbent article of claim 1, wherein the thickness of the absorbent pad is less than about 1.5 millimeters.

8. The absorbent article of claim 1, wherein the thickness of the absorbent pad is less than about 1 millimeter.

9. The absorbent article of claim 1, wherein the combined thickness of the outer cover, the body side liner, the absorbent pad, and any additional layers between the outer cover and the body side liner is less than about 2.5 millimeters.

10. The absorbent article of claim 1, wherein the combined thickness of the outer cover, the body side liner, the absorbent pad, and any additional layers between the outer cover and the body side liner is less than about 2 millimeters.

11. The absorbent article of claim 1, wherein the absorbent capacity is less than twice the anticipated single insult volume.

12. The absorbent article of claim 1, wherein the absorbent article provides less than 10% insult liquid volume runoff when the article is insulted with the anticipated single insult volume.

13. The absorbent article of claim 1, wherein the absorbent article has a total mass of less than 30 grams.

14. The absorbent article of claim 1, wherein the absorbent article has a total mass of less than 25 grams.

15. The absorbent article of claim 1, wherein the absorbent article has a total mass of less than 20 grams.

16. A disposable absorbent pant comprising:
a chassis defining a waist opening and first and second leg openings;
the chassis including at least a liquid-permeable body side liner, an absorbent pad and a substantially liquid-impermeable outer cover layer;
wherein the chassis has a thickness of less than about 3 millimeters, the absorbent pad alone has a thickness of less than about 2 millimeters, and the pant provides less than 15% insult liquid volume runoff when the pant is insulted with a anticipated single insult volume.

17. The disposable absorbent pant of claim 16, wherein the absorbent pad comprises superabsorbent and fluff pulp.

18. The disposable absorbent pant of claim 16, wherein the absorbent pad comprises multiple layers of superabsorbent.

19. The disposable absorbent pant of claim 16, wherein the absorbent pad comprises at least two different superabsorbent materials and each of the superabsorbent materials is located in a different location within the absorbent pad.

20. The disposable absorbent pant of claim 16, wherein the absorbent pad comprises a greater amount of superabsorbent in a first region of the absorbent pad and a lesser amount of superabsorbent in a second region of the absorbent pad.

21. The disposable absorbent pant of claim 16, further comprising a surge layer between the absorbent pad and the body side liner.

22. The disposable absorbent pant of claim 16, further comprising a pair of containment flaps attached to the chassis adjacent the leg openings.

23. The disposable absorbent pant of claim 16, further comprising a pair of leg elastics attached to the chassis adjacent the leg openings.

24. The disposable absorbent pant of claim 16, wherein the thickness of the absorbent pad is less than about 1.5 millimeters.

25. The disposable absorbent pant of claim 16, wherein the thickness of the absorbent pad is less than about 1 millimeter.

26. The disposable absorbent pant of claim 16, wherein the thickness of the chassis is less than about 2.5 millimeters.

27. The disposable absorbent pant of claim 16, wherein the thickness of the chassis is less than about 2 millimeters.

28. The disposable absorbent pant of claim 16, wherein the disposable absorbent pant provides less than 10% insult liquid volume runoff when the pant is insulted with the anticipated single insult volume.

29. The disposable absorbent pant of claim 16, having an absorbent capacity of less than three times the anticipated single insult volume.

30. The disposable absorbent pant of claim 16, having an absorbent capacity of less than twice the anticipated single insult volume.

31. The disposable absorbent pant of claim 16, wherein the disposable absorbent pant has a total mass of less than 30 grams.

32. The disposable absorbent pant of claim 16, wherein the disposable absorbent pant has a total mass of less than 25 grams.

33. The disposable absorbent pant of claim 16, wherein the disposable absorbent pant has a total mass of less than 20 grams.

34. A disposable absorbent pant comprising:
a chassis defining a waist opening and first and second leg openings;
the chassis including at least a liquid-permeable body side liner, an absorbent pad and a substantially liquid-impermeable outer cover layer;
wherein the chassis has a thickness of less than about 3 millimeters, the absorbent pad alone has a thickness of less than about 2 millimeters, and the pant has a saturation capacity of about 90% to about 150% of an anticipated single insult volume as determined by 0.5 psi saturation capacity, wherein the pant provides less than 15% insult liquid volume runoff when the pant is insulted with the anticipated single insult volume.

35. The disposable absorbent pant of claim 34, wherein the absorbent pad comprises superabsorbent and fluff pulp.

36. The disposable absorbent pant of claim 34, wherein the absorbent pad comprises multiple layers of superabsorbent.

37. The disposable absorbent pant of claim 34, wherein the absorbent pad comprises at least two different superabsorbent materials and each of the superabsorbent materials is located in a different location within the absorbent pad.

38. The disposable absorbent pant of claim 34, wherein the absorbent pad comprises a greater amount of superabsorbent in a first region of the absorbent pad and a lesser amount of superabsorbent in a second region of the absorbent pad.

39. The disposable absorbent pant of claim 34, wherein the thickness of the absorbent pad is less than about 1.5 millimeters.

40. The disposable absorbent pant of claim 34, wherein the thickness of the absorbent pad is less than about 1 millimeter.

41. The disposable absorbent pant of claim 34, wherein the thickness of the chassis is less than about 2.5 millimeters.

42. The disposable absorbent pant of claim 34, wherein the thickness of the chassis is less than about 2 millimeters.

43. The disposable absorbent pant of claim 34, wherein the pant provides less than 10% insult liquid volume runoff when the pant is insulted with the anticipated single insult volume.

44. The disposable absorbent pant of claim 34, having an absorbent capacity of less than twice the anticipated single insult volume.

45. The disposable absorbent pant of claim 34 comprising a single insult training pant.

46. The disposable absorbent pant of claim 34, wherein the disposable absorbent pant has a total mass of less than 30 grams.

47. The disposable absorbent pant of claim 34, wherein the disposable absorbent pant has a total mass of less than 25 grams.

48. The disposable absorbent pant of claim 34, wherein the disposable absorbent pant has a total mass of less than 20 grams.

49. A disposable absorbent article comprising:
an outer cover;
a body side liner at least partially bonded to the outer cover; and
an absorbent pad positioned between the outer cover and the body side liner, the absorbent pad having a thickness of less than about 2 millimeters;
the outer cover, the body side liner, the absorbent pad, and any additional layers between the outer cover and the body side liner, having a combined thickness of less than about 3 millimeters; and
the disposable absorbent article having an absorbent capacity of between about 30 grams and about 400 grams, wherein the disposable absorbent article has a saturated capacity between about 9 grams/gram and about 11 grams/gram.

50. The absorbent article of claim 49, wherein the absorbent pad comprises superabsorbent and fluff pulp.

51. The absorbent article of claim 49, wherein the absorbent pad comprises multiple layers of superabsorbent.

52. The absorbent article of claim 49, wherein the absorbent pad comprises at least two different superabsorbent materials and each of the superabsorbent materials is located in a different location within the absorbent pad.

53. The absorbent article of claim 49, wherein the absorbent pad comprises a greater amount of superabsorbent in a first region of the absorbent pad and a lesser amount of superabsorbent in a second region of the absorbent pad.

54. The absorbent article of claim 49, wherein the thickness of the absorbent pad is less than about 1.5 millimeters.

55. The absorbent article of claim 49, wherein the thickness of the absorbent pad is less than about 1 millimeter.

56. The absorbent article of claim 49, wherein the combined thickness of the outer cover, the body side liner, the absorbent pad, and any additional layers between the outer cover and the body side liner is less than about 2.5 millimeters.

57. The absorbent article of claim 49, wherein the combined thickness of the outer cover, the body side liner, the absorbent pad, and any additional layers between the outer cover and the body side liner is less than about 2 millimeters.

58. The absorbent article of claim 49, wherein the absorbent capacity is between about 40 grams and about 300 grams.

59. The absorbent article of claim 49, wherein the absorbent capacity is between about 50 grams and about 150 grams.

60. The absorbent article of claim 49, wherein the absorbent article has a total mass of less than 30 grams.

61. The absorbent article of claim 49, wherein the absorbent article has a total mass of less than 25 grams.

62. The absorbent article of claim 49, wherein the absorbent article has a total mass of less than 20 grams.

* * * * *

UNITED STATES PATENT AND TRADEMARK OFFICE
CERTIFICATE OF CORRECTION

| | | |
|---|---|---|
| PATENT NO. | : 7,615,040 B2 | Page 1 of 1 |
| APPLICATION NO. | : 10/025173 | |
| DATED | : November 10, 2009 | |
| INVENTOR(S) | : Olson et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 2350 days.

Signed and Sealed this

Nineteenth Day of October, 2010

David J. Kappos
*Director of the United States Patent and Trademark Office*